United States Patent [19]

Buckler

[11] Patent Number: 5,261,686
[45] Date of Patent: Nov. 16, 1993

[54] SEMI-RECUMBENT

[76] Inventor: Clive E. Buckler, S. 1408 Shamrock, Veradale, Wash. 99037

[21] Appl. No.: 864,465

[22] Filed: Apr. 6, 1992

[51] Int. Cl.⁵ ............................................. B62K 3/02
[52] U.S. Cl. ................................. 280/274; 280/281.1; 280/288.1
[58] Field of Search ................... 280/274, 278, 281.1, 280/282, 284, 287, 288.1

[56] References Cited

U.S. PATENT DOCUMENTS

| | | | |
|---|---|---|---|
| 640,680 | 1/1900 | Merrow | 280/260 |
| 709,718 | 9/1902 | Monahan | 280/284 |
| 1,056,492 | 3/1913 | Bilsten | 280/284 |
| 2,482,472 | 9/1949 | Fried | 280/261 |
| 4,129,317 | 12/1978 | Bell | 280/274 |
| 4,336,664 | 6/1982 | Turner et al. | 280/261 |
| 4,432,561 | 2/1984 | Feikema et al. | 280/288.1 |
| 4,453,730 | 6/1984 | Klose | 280/274 |
| 4,502,705 | 3/1985 | Weaver | 280/288.1 |
| 4,592,563 | 6/1986 | Dean et al. | 280/253 |
| 4,618,160 | 10/1986 | McElfresh | 280/288.1 |
| 4,659,098 | 4/1987 | Jacobson | 280/288.1 |
| 4,878,684 | 11/1989 | Lemle | 280/288.1 |
| 4,925,203 | 5/1990 | Buckler | 280/278 |

FOREIGN PATENT DOCUMENTS

| | | | |
|---|---|---|---|
| 3335285 | 2/1984 | Fed. Rep. of Germany | 280/288.1 |
| 286409 | 2/1965 | Netherlands | |
| 8898 | 6/1897 | Sweden | 280/274 |
| 6748 | 3/1896 | United Kingdom | |
| 1462154 | 1/1977 | United Kingdom | |

OTHER PUBLICATIONS

Add; Associate Dynamics Inc., 15510 Wright Brothers Dr., Addison.

Primary Examiner—Margaret A. Focarino
Assistant Examiner—Kevin Hurley

[57] ABSTRACT

A two wheel bicycle on which the rider sits elevated above and slightly forward of the rear wheel on a highback seat. The seat is supported by the rearward end of a multiple angled main tube. The position of the pedal crank assembly is forward and upward of the pedal crank position of conventional bicycles and downward and rearward of that normally associated with fully recumbent bicycles relative to the seat. The rider steers by way of long upwardly curved handlebars affixed to an elongated multiple angled steering stem originating in a front steering head tube assembly and extending rearward in general parallel alignment with the multiple angled main tube. The steering stem extends upward and rearward terminating under the area of the rider's upper legs. The multiple angled main tube attaches at a forward portion thereof to the head tube and extends rearward therefrom in a generally horizontal plane for a distance prior to turning relatively sharply upward near the rear wheel, and continues extending upward and rearward at an approximately 45 degree angle. The main tube is fitted with an inner member telescopically slidable, and the slidable member being positioned above the rear wheel supports the seat in a adjustable manner. The elongated steering stem is positioned above the main tube and follows the approximate angled path as the main tube and thereby the bicycle is provided with a low step-over height for the rider to straddle and mount or dismount the bike.

9 Claims, 11 Drawing Sheets

SEMI-RECUMBENT

BACKGROUND OF THE INVENTION

1. Field of the Invention

This invention relates to two-wheel manually powered bicycles in general, and more particularly to an improved semi-recumbent bicycle. My prior U.S. Pat. No. 4,925,203 issued May 15, 1990 for a "Semi-recumbent Bicycle with Adjustable Frame" is incorporated herein by reference for both essential and nonessential material.

2. Description of the Prior Art

With a semi-recumbent bicycle, the pedal crank assembly is more forward and upward relative to the seat than that of the pedal crank assembly of more conventional bicycles such as multi-speed racing bicycles and mountain style bicycles where the pedal assembly is essentially vertically downward from the seat. The pedal crank assembly of a semi-recumbent bicycle is also somewhat downward and rearward of that associated with fully recumbent bicycles. With a semi-recumbent bicycle, the rider sits in a high-backed seat in a semi-recumbent position elevated above the rear wheel and steers by way of handlebars originating under the area of the rider's upper legs. The legs of the rider of a semi-recumbent extend forward and somewhat downward from the seat to the pedals, while the legs of the rider of a fully recumbent bicycle extend generally straight forward or in some cases even slightly upward from a high-backed seat to the pedals.

A problem associated with many prior art bicycles is the position of the pedals relative to the seat. This seat-to-pedal relationship is primarily what determines the degree of pedal pushing power a given rider can develope. Fully recumbent bicycles have a good seat-to-pedal relationship as far as development of power is concerned, but the vertical height at which the rider sits on these bicycles presents significant safety problems, as sitting quite low (forward and downward of the top of the rear wheel) in a fully recumbent bicycle makes it difficult for both the rider and automobile drivers to detect the presence of each other over and around other vehicles. Low visibility can lead to serious accidents. A significant problem with the pedal positions associated with many fully recumbent bicycles, which does not exist with semi-recumbent bicycles, is that with fully recumbents, the rider's legs are normally extending straight out or even slightly upward in front of him with his feet on the pedals, and the effect of gravity is such that the feet, when not in the pushing mode, have a tendency to slip downward and off of the pedals. Although systems which clip or fasten the feet (shoes) to the pedals are known, many feel such shoe-to-pedal fastening systems create more problems than they solve since if one cannot get his feet off of the pedals and to the ground quick enough, one could easily fall and be seriously injured. A semi-recumbent bicycle allows for pushing against a high-backed seat, and therefore the development of high pedal pushing power, without the problem of the feet sliding downward off of the pedals, and this being due to the angle of approach of the rider's legs and feet to the pedals.

The high power which can be applied by pushing on the pedals with a fully recumbent or semi-recumbent bicycle is dependant on high-backed seats which the rider can push against, in combination with the pedals being of the proper distance from the seat back for the particular rider's leg length. If the pedals are too far from or too close to the seat back for a particular rider's leg length, significant pushing power can be lost, and therefore proper seat positioning (distance) relative to the pedals is important for the development of power.

Seat re-positioning or fine tuning of the positioning thereof for a particular rider is not a significant problem in fully recumbent bicycles since in most cases adjustments to the seat position relative to the pedals simply involves sliding the seat one way or the other horizontally on a horizontally disposed main frame member of the bicycle to either position the seat closer or further from the pedals.

Proper seat positioning on semi-recumbent bicycles is somewhat more difficult than with fully recumbents, as with semi-recumbents the seat adjustment is ideally provided with both vertical and horizontal adjustments to the seat relative to the pedals. With a semi-recumbent which relies on the angle of approach of the rider's legs and feet to the pedals to help maintain his feet on the pedals when not in the pushing mode, if the seat were to be re-positioned straight rearward only, or straight upward only, the angle of approach of the rider's legs and feet to the pedals would be changed, and although this angular change in some instances is insignificant and maybe even desirable, in some situations it is significant and undesirable, and therefore ideally, the rider is given a choice of mixing vertical and horizontal seat adjustments.

Although a structural solution to such seat adjustments for a semi-recumbent is disclosed in my U.S. Pat. No. 4,925,203, that which is taught in my patent is a frame for a semi-recumbent which requires a relatively high step-over for the rider to mount or dismount the bicycle. The frame of my bicycle of the reference patent allows for simple seat position adjustments, wherein independent vertical and horizontal adjustments to the seat position relative to the pedals may be accomplished. The frame disclosed in my prior patent includes a steeply angled, but otherwise straight top tube which attaches at the forward end thereof to the head tube, and then extends at a steep upward elevation to above the rear wheel. The steeply angled top tube of my prior art bike is telescopic to provide for length adjustment, and has a seat post and seat affixed to the rearward upper end of the top tube. The telescopic nature of the angled top tube allows for horizontal positioning the seat closer or further from the pedals, and due to the angled nature of the top tube, lengthening or shortening the top tube also changes the vertical height of the seat. The vertically positioned seat post of my prior art bike is releasibly retained in a clamp which allows for vertical adjustments of the seat position independent of the horizontal adjustment provided by the telescopic top tube. The semi-recumbent bicycle of my previous patent additionally includes an elongated steering stem extending from the upper end of the head tube rearward in general parallel alignment with the steeply angled top tube to support U-shaped handlebars. With the semi-recumbent bicycle of the reference patent, the steering stem extends rearward toward the seat underneath and between the rider's legs, with the wide upwardly turned U-shaped handlebars extending upward around the rider's legs, one portion or arm of the handlebars being positioned on the exterior side of each of the rider's legs. The steering stem is positioned above the angled top tube, and due to the position, and straight but steeply angled structure of this top tube, the steering stem is required for clearance purposes to be positioned relatively high above the ground and thereby requires the rider to straddle what is a relatively high steering stem to mount or dismount the bicycle. Riders having long legs have little problem mounting a given size bicycle of my previous patent, however riders having short legs may have some difficulty with the same size bicycle.

In order to mount a semi-recumbent bicycle such as that of my previous patent, and also the improved semi-recumbent bicycle of this disclosure for that matter, the rider first straddles the elongated steering stem with one leg on each side thereof, which if the steering stem is too high relative to the rider's leg length and thus crotch, is difficult and can be painful. The rider is positioned with his feet on the ground and is facing forward toward the front of the bike. The rider holds the bike stable by holding the handlebars with both hands, as one end portion of the handlebars is positioned on each side of the rider's upper body. The seat of the bike is positioned directly behind and slightly above the rider's buttocks at this point. One pedal crank with pedal is rotated downward (preferably earlier in the procedure), and the rider places one foot on this downward pedal while stabilizing himself and the bike with the other foot still on the ground. The rider then pushes with his other foot against the ground to begin the bike rolling forward, at which time the foot resting on the pedal is pushed against so as to use the low pedal as a step as the rider lifts his other foot from the ground and lifts himself relative to the bike seat directly behind him. The rider moves his buttocks toward and first upward and then downward into the seat as the bike continues to slowly roll, and places the other foot against the opposite pedal to begin pedaling and thus riding the bicycle. To dismount the bike, the rider slows the bike and while still holding onto the handlebars, he slides off of the seat to land with one or both feet on the ground and with his legs straddling the steering stem. Hand brakes on the handlebars are convenient during both mounting and dismounting.

In attempting to address the high step-over associated with the semi-recumbent bicycle of my previous U.S. Pat. No. 4,925,203, a relatively small front wheel (16 inch) was used which resulted in lowering the steering stem which the rider had to straddle while mounting or dismounting the bike. Although the small front wheel resulted in lowering the step-over height and thus making a given size bike mountable and dismountable by a larger variety of sizes of riders having different leg lengths, the relatively small front wheel also resulted in new problems which could be eliminated if a larger front wheel could be used. A larger front wheel would give greater speed potential due to lower rolling resistance, and improved handling under most circumstances during riding. Additionally, there is currently a greater number of high quality larger bike tires (20 inch or larger) on the market today from which to choose than there are smaller (16 inch) or smaller tires, since there is relatively little demand for high or professional quality very small bike rims and tires. Most if not all of the available small bike rims and tires are made for children's bicycles, and are usually not of the highest quality.

It is desireable to have a given size of semi-recumbent bicycle fit a variety of riders to reduce the number of bicycle sizes which need to be manufactured and shipped in a commercial operation, and additionally to provide the necessary seat position fine tuning adjustment capabilities as previously mentioned, and further to provide a semi-recumbent bicycle which handles well during riding.

SUMMARY OF THE INVENTION

The improved semi-recumbent bicycle of this disclosure solves many of the problems associated with prior art semi-recumbents including the semi-recumbent bicycle of my U.S. Pat. No. 4,925,203 which is herein incorporated by reference for both essential and nonessential material. A semi-recumbent bicycle of a single given size and built in accordance with the present invention will fit a variety of riders and thereby reduces the number of bicycle sizes which need to be manufactured to accommodate all riders, and additionally provides the necessary seat position adjustment capabilities for fine tuning the position of the seat relative to the pedals, and further provides a semi-recumbent bicycle which handles well since a relatively large front wheel such as a 20 inch may be used if desired, while still having a low step-over height to straddle during mounting or dismounting of the bike.

The semi-recumbent bicycle of this disclosure may include bolt-in or replaceable seat and chain stays, and may also include pivotal connections in the chain stays and a shock-absorber seat stay arrangement to suspend the rear wheel as is taught in the reference patent. Additionally, a bicycle in accordance with the present invention is of a sturdy design which is relatively quick and inexpensive to manufacture.

It is therefor a primary object of my invention to provide an improved semi-recumbent bicycle wherein the seat is positioned above the rear wheel to elevate the rider, and the handlebars originate underneath the rider's upper legs, with the handlebars being supported by an elongated steering stem extending from the top of the head tube and extending rearward toward the seat in a relatively low elevation to the ground in order to provide a low step-over height for a person to straddle during mounting or dismounting of the bike. The lower steering stem position being allowed by a main tube having multiple angles wherein a forward portion thereof is positioned below the low portion of the steering stem and is also positioned at a relatively low elevation relative to the ground.

It is a further object of my invention to provide the above in an improved semi-recumbent bicycle which includes horizontal seat positioning capabilities and vertical seat positioning capabilities which may be utilized independent of one another.

It is an even further object of my invention to provide the above in an improved semi-recumbent bicycle which allows for the use of a relatively large front wheel if desired, while still providing for the relatively low step-over height.

It is a still further object of my invention to provide the above in an improved semi-recumbent bicycle wherein the pedal position relative to the seat is such that a rider sits in a semi-recumbent position with his legs approaching the pedals in a downward and forwardly extending angle, with the angle being such that the rider is positioned to be able to push against a high-back of the seat, and further that the effect of gravity does not work to pull the rider's feet downward and off of the pedals when the rider is not in the pedal pushing mode.

It is an even still further object of my invention to provide the above in an improved semi-recumbent bicycle wherein a relative few sizes of the bicycle in accordance with the present invention may be manufactured to accommodate a large variety of rider sizes, and may optionally utilize readily changeable bolt-in seat and chain stays, and shock absorbers.

Structures and principles of my invention will be better understood with a reading of the reference patent and of the below remaining specification along with examination of my drawings of structural embodiments of the invention shown and described for example. The drawing figures and the Description Of The Preferred Embodiments are illustrative and descriptive of structures and principles which may be incorporated in a number of slightly different semi-recumbent bicycles, all of which are in accordance with the present invention. The drawings and written description are given only for example in order to allow those skilled in the art to be able to both build and use at least one semi-recumbent bicycle in accordance with the present invention, and are not to limit the scope of the invention only to the specific structural embodiments detailed.

DESCRIPTION OF THE PREFERRED EMBODIMENTS

In drawing FIGS. 2 through 11, various closely related embodiments 200, 200A and 200B of my semi-recumbent bicycle in accordance with the present invention, and some individual components (FIGS. 9, 10 and 11) thereof are shown. Multiple slightly varied embodiments of bikes are shown simply to illustrate some, but not all of the possibilities within the scope of the present invention. In all embodiments of my bicycle, multiple gearing may or may not be used. All versions of my bicycles may be equipped with known braking systems using caliper or drum brakes operational by brake cables and brake levers or other suitable braking systems such as hydraulic brakes. The braking may be applied to either the front wheel, the rear wheel or both.

Figure 1:
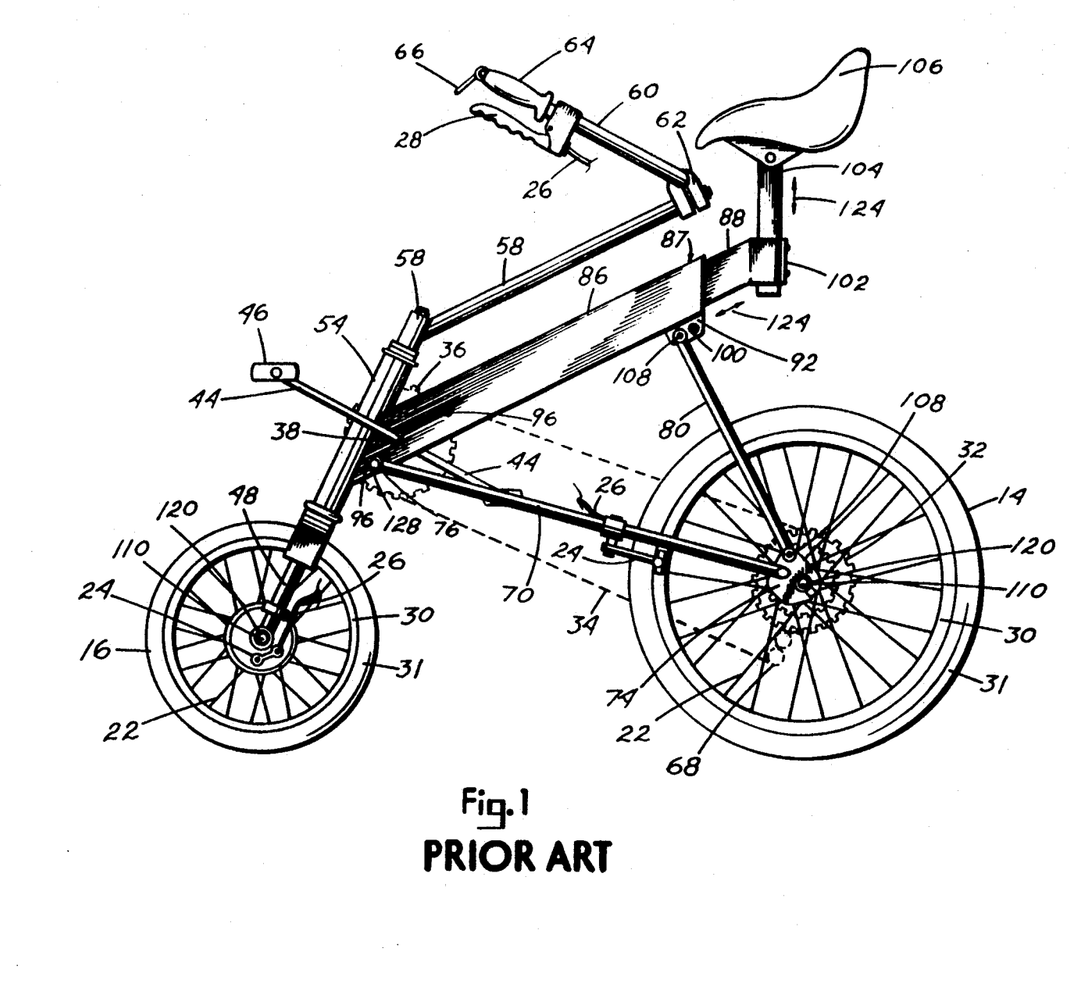
FIG. 1 is a left side view of my prior art semi-recumbent bicycle in accordance with the reference patent.

In FIG. 1, my prior art semi-recumbent bike of the reference patent is shown, and it may readily seen that the steering stem 58 is positioned at a rather steep and elevated angle relative to the ground, and necessarily so in order to gain clearance above the angled tube top 86. The angled tube top 86 is a straight telescopic member affixed at an angle to head tube 54. As previously stated, a relatively small diameter front wheel 16 is used to lower the overall height of the steering stem 58 of my prior art bike, and thus allow a larger variety of rider's to mount a given size bike in accordance with the prior art bike of the reference patent.

Figure 2:
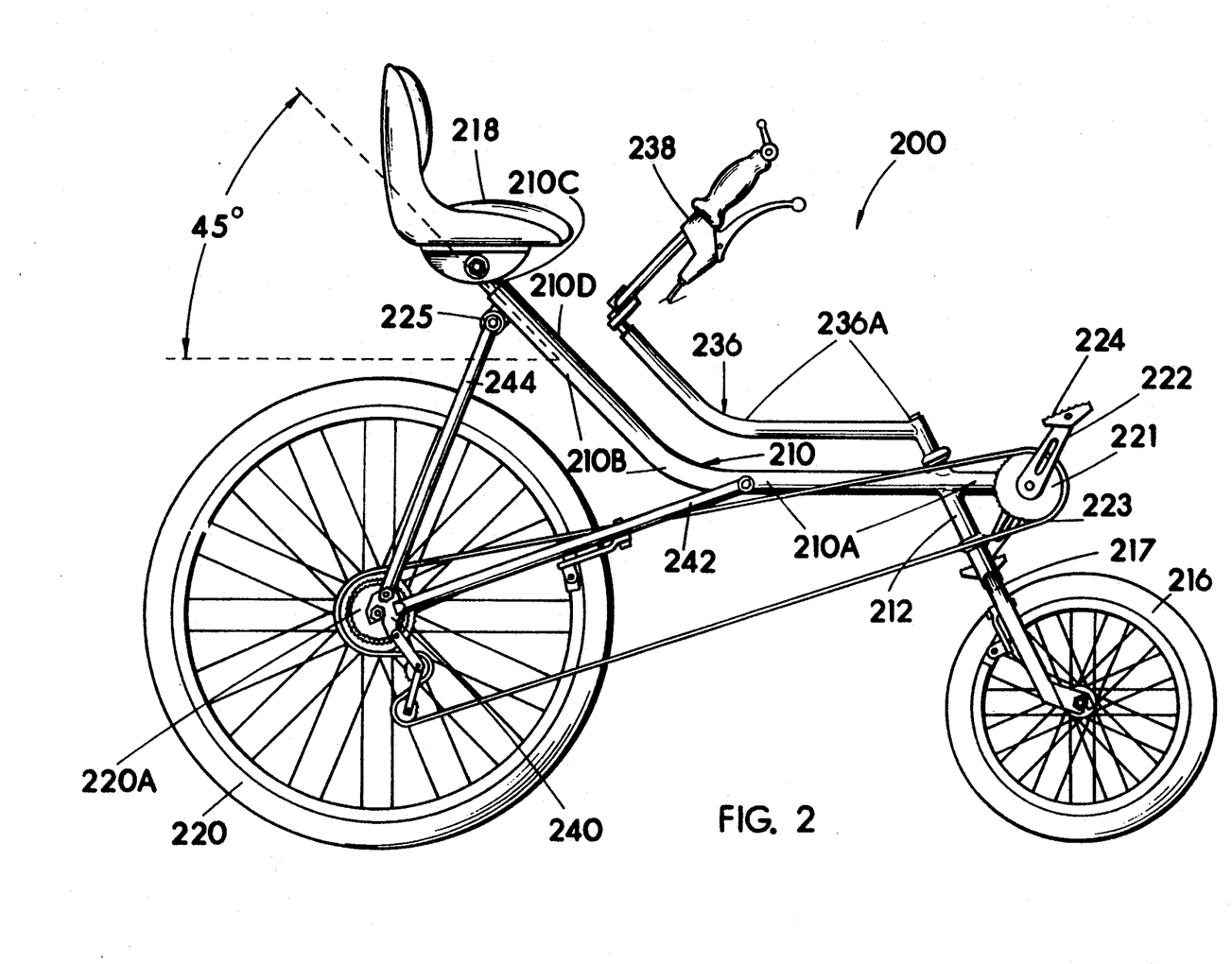
FIG. 2 is a right side view of a first embodiment of a semi-recumbent bicycle in accordance with the present invention.
Figure 3:
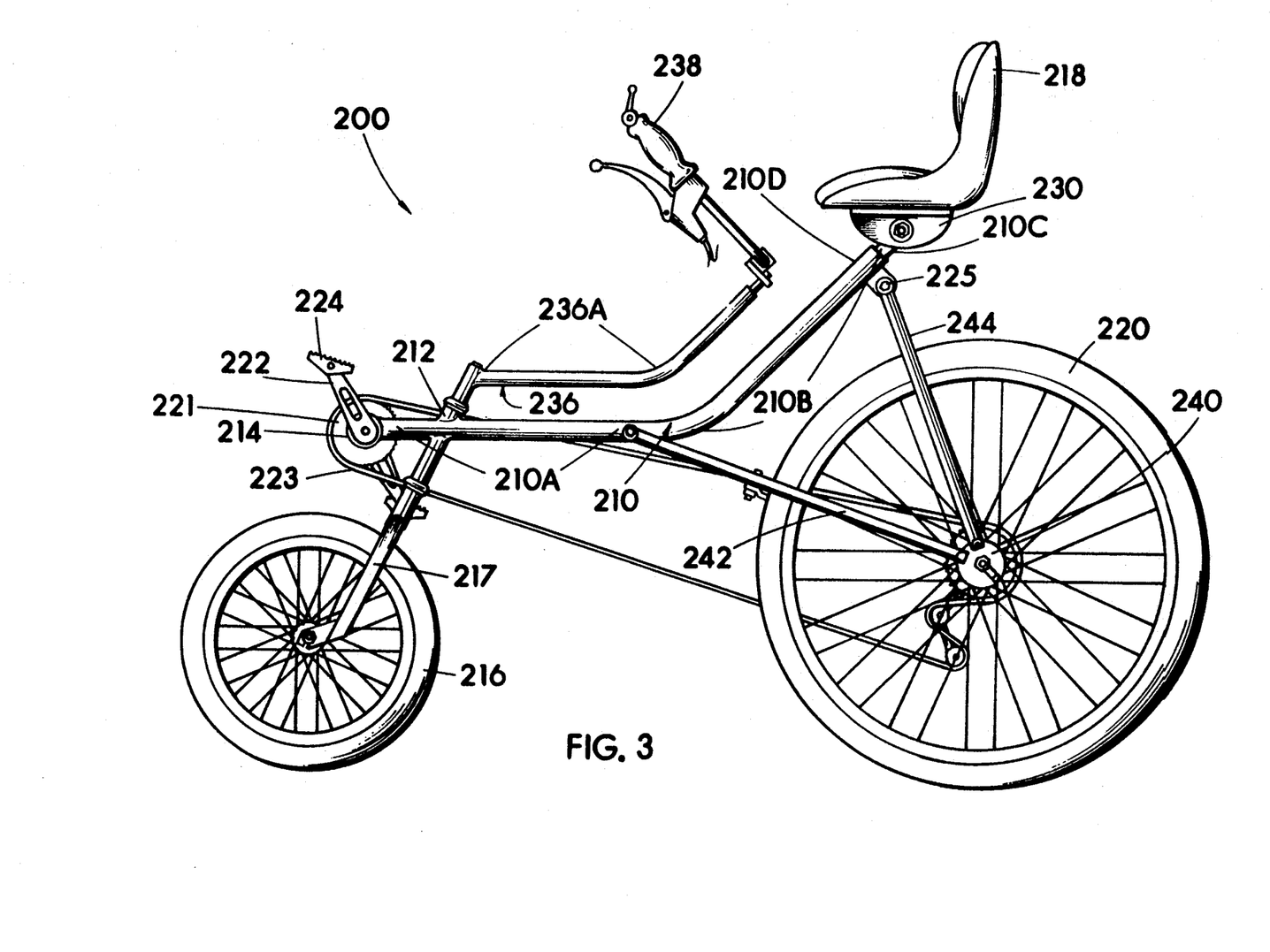
FIG. 3 is a left side view of the bike of FIG. 2.

FIGS. 2 and 3 are the right and left sides of a first embodiment bike 200 which essentially typifies the present invention. In the present invention as illustrated in FIGS. 2 and 3, an elongated main tube 210 is essentially a replacement of angled top tube 86 of the prior art bike of FIG. 1 of the reference patent. Main tube 210 is essentially a multiply angled equivalent to the straight, angled top tube 86. Main tube 210 may be made of any suitably rigid and strong material such as steel, aluminum, titanium, plastics or composite materials for example. An elongated, generally horizontally disposed forward portion 210A of main tube 210 attaches to a head tube 212, and as may be ascertained from the drawings, main tube 210 may extend a distance forward beyond head tube 212 in order to provide a position to attach a bottom bracket 214 above front wheel 216 as shown in FIG. 3. Head tube 212 has been passed through a drilled or otherwise fashioned vertical hole through main tube 210 prior to being welded in place. The major length of main tube 210 extends rearward from head tube 212 toward the rear wheel 220 and seat 218. Head tube 212 and main tube 210 in combination, essentially define the main framework of the bike, and forward portion 210A of main tube 210 adjacent to and in combination with head tube 212 defines a forward portion of the main framework which in turn correlates with what is considered the front or forward end of the bike. Bottom bracket 214 contains bearings or bushings supporting a crank spindle or axle which in turn supports two oppositely disposed crank arms 222 with attached pedals 224, and at least one front sprocket 221 which is connected by a drive chain 223 to a rear sprocket 220A on the rear wheel 220. Bottom bracket 214 could be placed closer toward head tube 212 as illustrated in the reference patent, however that which is shown in FIG. 2 and 3 with the bottom bracket 214 attached to the terminal end of main tube 210 forward of head tube 212 provides a strong structure which is relatively simple to manufacture. The placement of bottom bracket 214 should be such that when taking into account the diameter of front wheel 216, and the length and outward angle or lack thereof of the crank arms 222, that clearance is provided between the cranks 222 with pedals 224 and the front wheel 216 with rotation of the crank arms 222 during riding, otherwise interference with turning the bike during riding can occur.

As may be ascertained from the drawings, main tube 210 has a second portion 210B which is rearward of the first portion 210A and substantially more vertically oriented. Main tube 210 changes angle between head tube 212 and rear wheel 220 from the generally horizontally disposed plane of forward portion 210A to the second substantially more vertically oriented plane of second portion 210B of main tube 210. From the angle change in main tube 210, second portion 210B extends upward and rearward to above rear wheel 220 to where seat 218 is attached to the upper rearward end main tube 210. In the specific example of main tube 210 in FIG. 2 and 3 of first embodiment 200, main tube 210 is made of round metal tubing wherein a bend in the tubing has been applied in order to provide the first and second planes, or multiple angles of the main tube 210. Bending a main tube 210 to achieve the first and second planes is relatively inexpensive with round tubing, and is normally quite strong.

Figure 6:
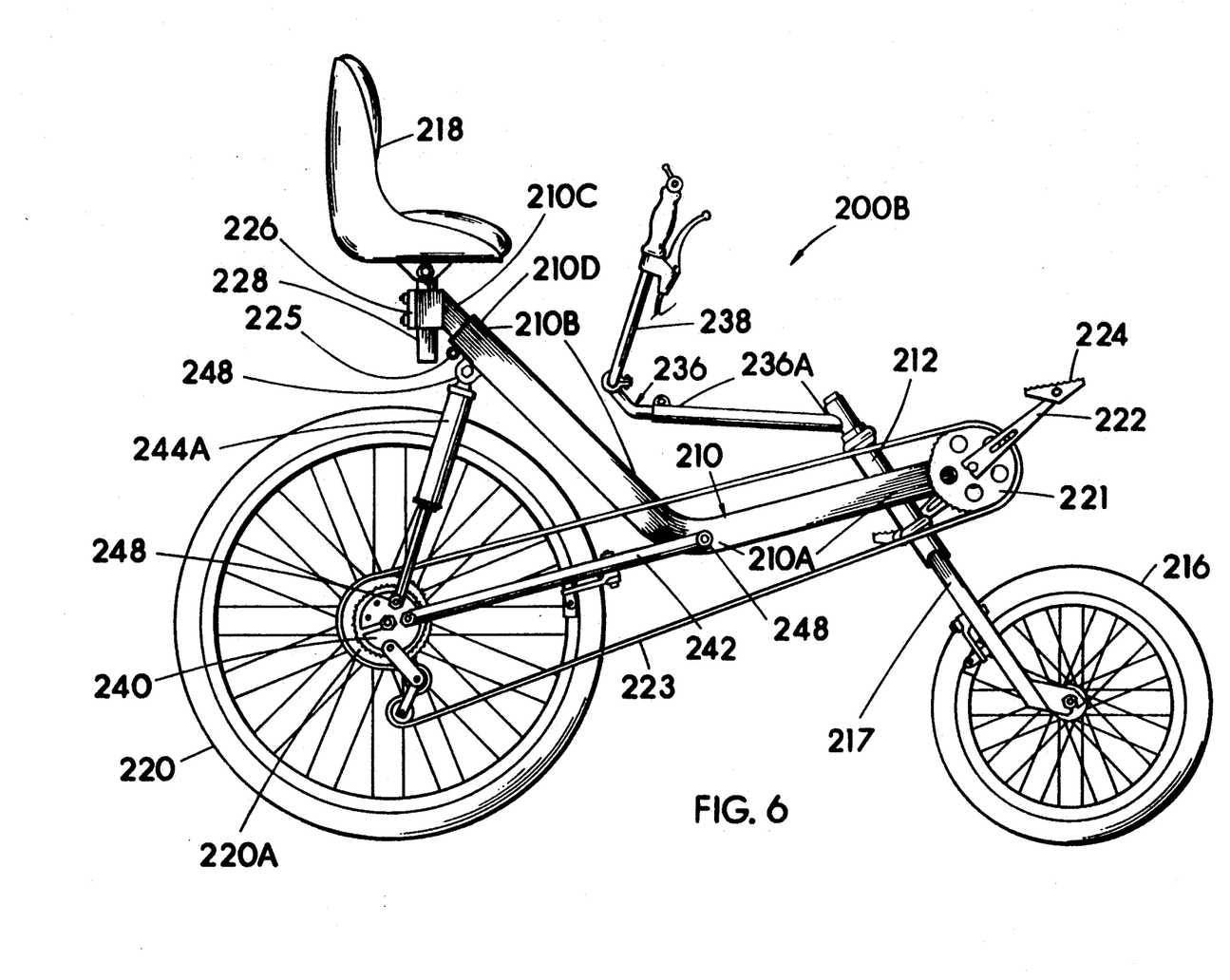
FIG. 6 is a right side view of a third embodiment of semi-recumbent bicycle in accordance with the present invention.
Figure 7:
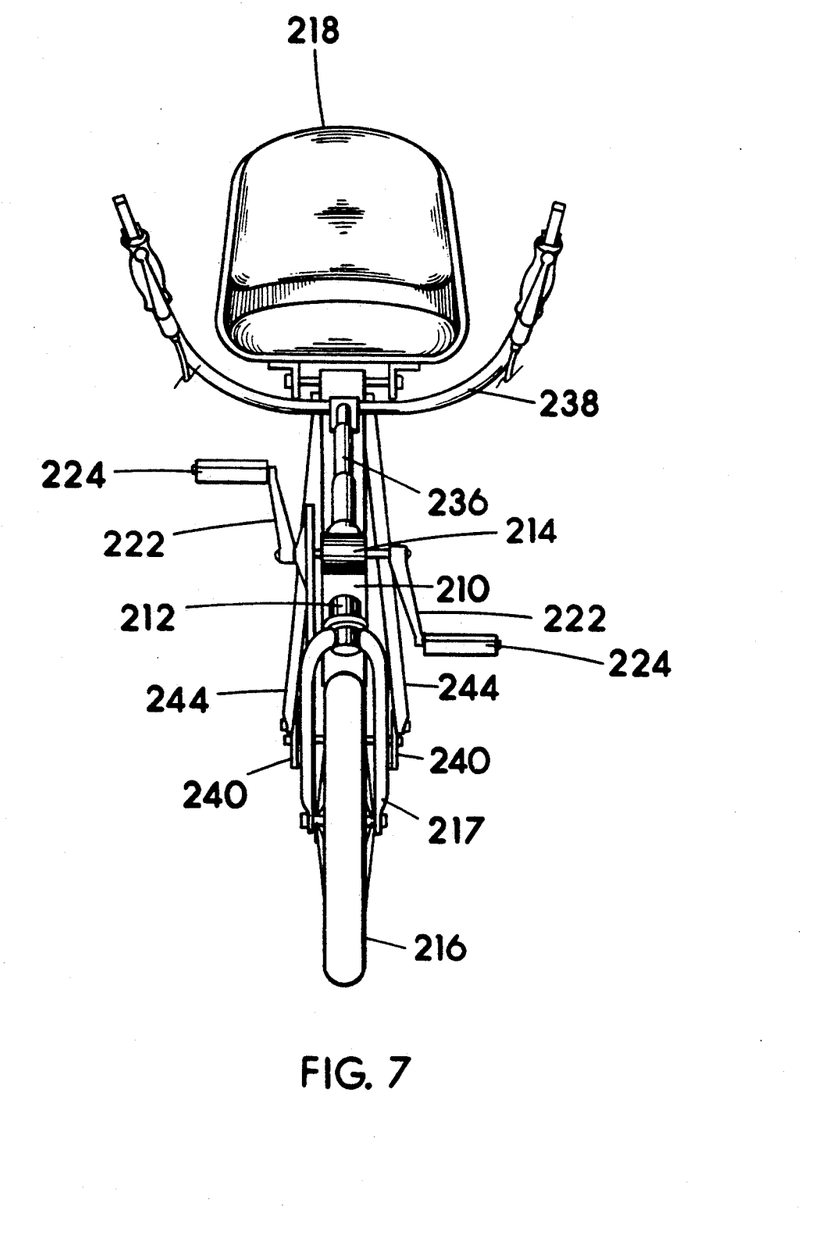
FIG. 7 is a front view of what is generally representative of any of the bikes in accordance with the present invention.
Figure 8:
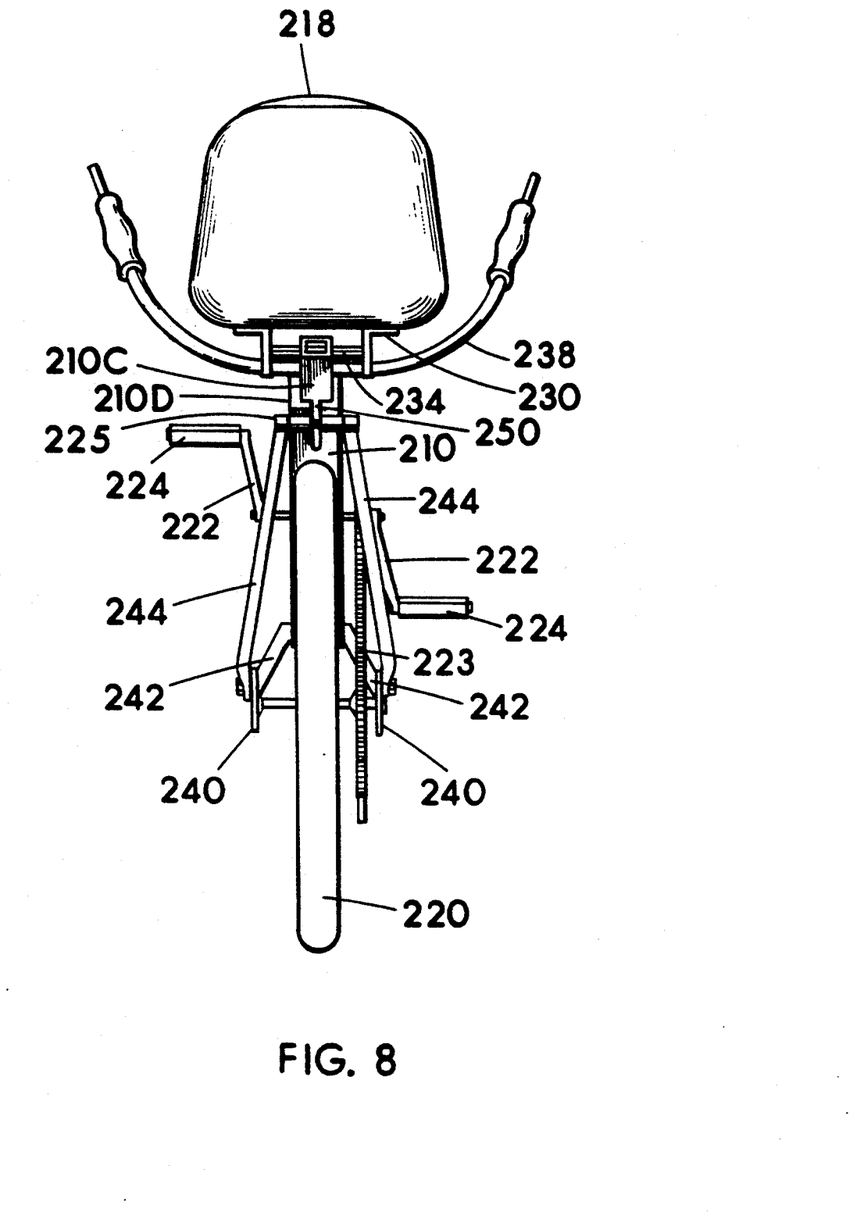
FIG. 8 is a rear view of what is generally representative of any of the bikes in accordance with the present invention.
Figure 9:
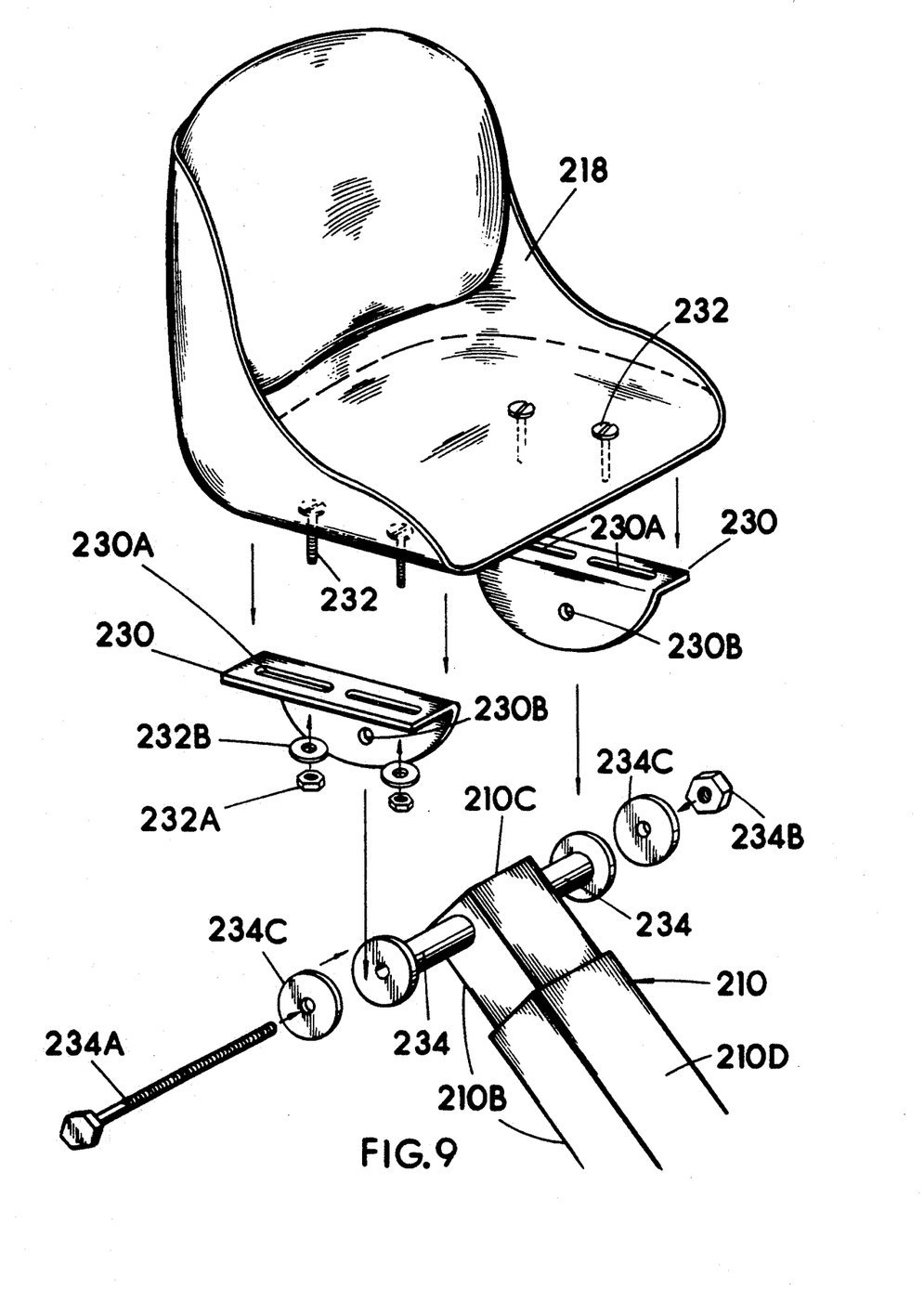
FIG. 9 is an enlarged view of a high-backed seat and adjustable attachment structure therefore.

Main tube 210 being similar to angled top tube 86 of FIG. 1 of my prior art bike of the reference patent, also preferably uses a telescopic arrangement which in this example includes an elongated inner member 210C within the upper rearward end of main tube 210, and more accurately within the outer portion 210D of second portion 210B. The inner member 210C is moveable inward and outward within second portion 210B, and seat 218 is attached to the inner member 210C of second portion 210B. As shown in considerable detail in FIG. 10, a releasable clamp structure 225 is formed at the top end of the outer portion 210D of main tube 210 in second portion 210B thereof, so as to render the inner member 210C stationary relative to the outer member 210D when the length of main tube 210 is adjusted to satisfaction. Second portion 210B of the main tube 210 is ideally placed at a 45 degree angle from horizontal as is indicated in FIG. 2 with dotted lines for illustrative purposes. A 45 degree angle provides a one-to-one ratio of elevational to horizontal movement of the seat 218 relative to the pedals 224 when lengthening or shortening main tube 210. The one-to-one ratio holds true when the inner member 210C is inserted or withdrawn relative to outer portion 210D. Although angles other than 45 degree angles do not provide the one-to-one ratio of elevational to horizontal changes to the position of seat 218, angles within a range of 30 to 70 degrees from horizontal with the second portion 210B extending upward and rearward over the rear wheel, do provide similar useful benefits, that is, a given amount of elevational change also results in a significant horizontal change to the position of seat 218. Second portion 210B of main tube 210 should be positioned within a range of 30 to 70 degrees from horizontal, and is ideally at a 45 degree angle. The upward and rearwardly angled second portion 210B provides both elevational and horizontal seat position choice by way of its telescopic nature, but not elevational and horizontal seat position choice independent of one another. Independent seat position adjustment capabilities wherein the horizontal position of the seat 218 relative to the pedals 224 may be changed without effecting the vertical height of the seat 218 relative to the pedals and ground is an optimum seat adjustment arrangement on a semi-recumbent bike of this nature, and assists in allowing a given size of bike of this nature be adjusted to fit a larger variety of rider sizes. Since the telescopic nature of main tube 210 does not alone provide for such independent seat adjustments, seat 218 may be attached to main tube 210 by way of a releasable clamp 226 attached on the terminal end of inner member 210C and supporting a vertically adjustable seat post 228 as shown in FIG. 6 of this disclosure, and described in the reference patent. As an alternative to the vertically adjustable seat post 228 shown in FIG. 6, as may be ascertained from FIG. 9, seat 218 may also be attached to the main tube 210 using two angled brackets 230 which have elongated slots 230A to accept seat retaining bolts 232, with bolts 232 passing downward through apertures through the seat 218. The bolts 232 are passed through the elongated slots 230A of brackets 230, and nuts 232A and washers 232B are applied to fasten the seat to the angled brackets. The elongated slots 230A are positioned extending lengthwise toward the front of the bike, and if the nuts 232A were to be loosened, the seat 218 could be positioned either directly forward or rearward horizontally relative the angled brackets 230 and to the pedals 224 without effecting elevation, and in this arrangement, the telescopic nature of main tube 210 would provide the vertical height adjustment with a degree of horizontal height adjustment. The two angled brackets 230 could be attached to tubular stems 234 welded to oppositely disposed sides of inner member 210C, and further by using a single long bolt 234A and a nut 234B with washers 234C to fasten brackets 230 to tubular stems 234. Bolt 234A would pass through apertures 230B in the lower portion of angled brackets 232 which would be abutted against the widened end of tubular stems 234 as may be ascertained from FIG. 8 and 9.

Tubular stem 234 in this situation would also serve to prevent the inner member from ever slipping excessively into the outer portion 210D of main tube 210. The attachment of angled brackets 230 to tubular stems 234 using a single long bolt 234A would allow for loosening of the nut 234B, and changing the angle of the seat 218 (to lean forward or rearward) if desired. It should be noted that other seat attachment structures could be used within the scope of the invention.

Front wheel 216 is supported by front forks 217. As is known, a tubular upper portion of the forks 217 is positioned within head tube 212, and is connected to a vertically oriented portion of steering stem 236 within the head tube 212 so that rotation of the steering stem 236 equates to turning the front wheel 216 for steering of the bike by the rider. Steering stem 236 has an elongated first portion 236A which extends rearward from above head tube 212 in a generally horizontally disposed plane toward seat 218. The horizontally disposed plane of first portion 236A is a relatively low plane or elevation relative to the ground, and is allowed by the clear space provided by the forward portion 210A of the main tube 210 being placed in a relatively low plane or elevation relative to the ground. The second portion 210B of main tube 210 which exists in a substantially more vertically oriented plane than the forward portion 210A of the main tube 210 is to allow the positioning of, and the support of the seat 218 upward above the rear wheel 220, which elevates the rider relative to both the ground and the lower placed pedal 224, which has advantages such as improved visibility by and of the rider, and also assists in providing the proper angular approach of the rider's legs to the pedals so he may develope maximum pushing power without his feet having the tendency to slip off of the pedals.

Steering stem 236 may terminate in its generally horizontal plane as may be ascertained from FIG. 6, or may be bent or otherwise angled to extend further rearward and or upward as is shown in FIG. 2. Handlebar 238 is attached to the rearward end of steering stem 236, and the position of handlebar 238 is normally always somewhat adjacent the seat 218, however, depending on the rider's choice, the handlebar 238 may be angled forward or rearward to position the upper terminal ends closer or further relative to seat 218 and rider. Handlebar 238 is a generally U-shaped handlebar having a rather wide spread. The handlebar 238 originates from its attachment to steering stem 236 underneath a rider's upper legs, and then the handlebar 238 extends outward and upward so as to position an end portion of the handlebar 238 disposed on each exterior side of the rider's legs. Steering stem 236 may be telescopic as is described in the reference patent and shown in the FIG. 2 drawing of the reference patent.

The length of the first portion of steering stem 236 needs to be significant relative to the thickness from front to rear of a human body, and this being due to the procedure to mount and dismount a bike of this nature wherein a person straddles steering stem 236 facing forward, and needs to be positioned somewhat rearward of the pedal 224 and forward of the attachment of handlebars 238 to the rearward end of steering stem 236. A person straddling steering stem 236 would be normally in about the center of the first portion 236A, although individual riders straddle the steering stem in slightly varied locations. The first portion 236A of steering stem 236 need not be perfectly horizontal, and the forward portion 210A of main tube 210 need not be perfectly horizontal below the first portion 236A of steering stem 236, they need only be generally horizontal or relatively low in elevation as may be ascertained from the drawings.

Rear wheel 220 at the rear or rearward end of the bike may be a conventional bike wheel comprising a rim, spokes, center hub and axle, and pneumatic tire. The axle would be supported by axle drop-out plates 240. The axle drop-out plates 240 are affixed to and supported by chain stays 242 and seat stays 244. Each of the chain stays 242 and seat stays 244 is additionally attached to the main framework of the bike, with the seat stays 244 preferably attached to main tube 210 up by the seat 218, and the chain stays 242 preferably attached near the angle change in main tube 210. The chain stays 242 could be attached to the head tube 212 as may be ascertained from FIG. 19 of the reference patent. The chain stays 242 and seat stays 244 should be attached to the main framework in a spaced relationship so as to define a triangle between the chain stays 242, seat stays 244, and main framework (main tube 210 in combination with head tube 212) as shown in FIG. 2 and 3, simply for structural strength and rigidity.

Figure 4:
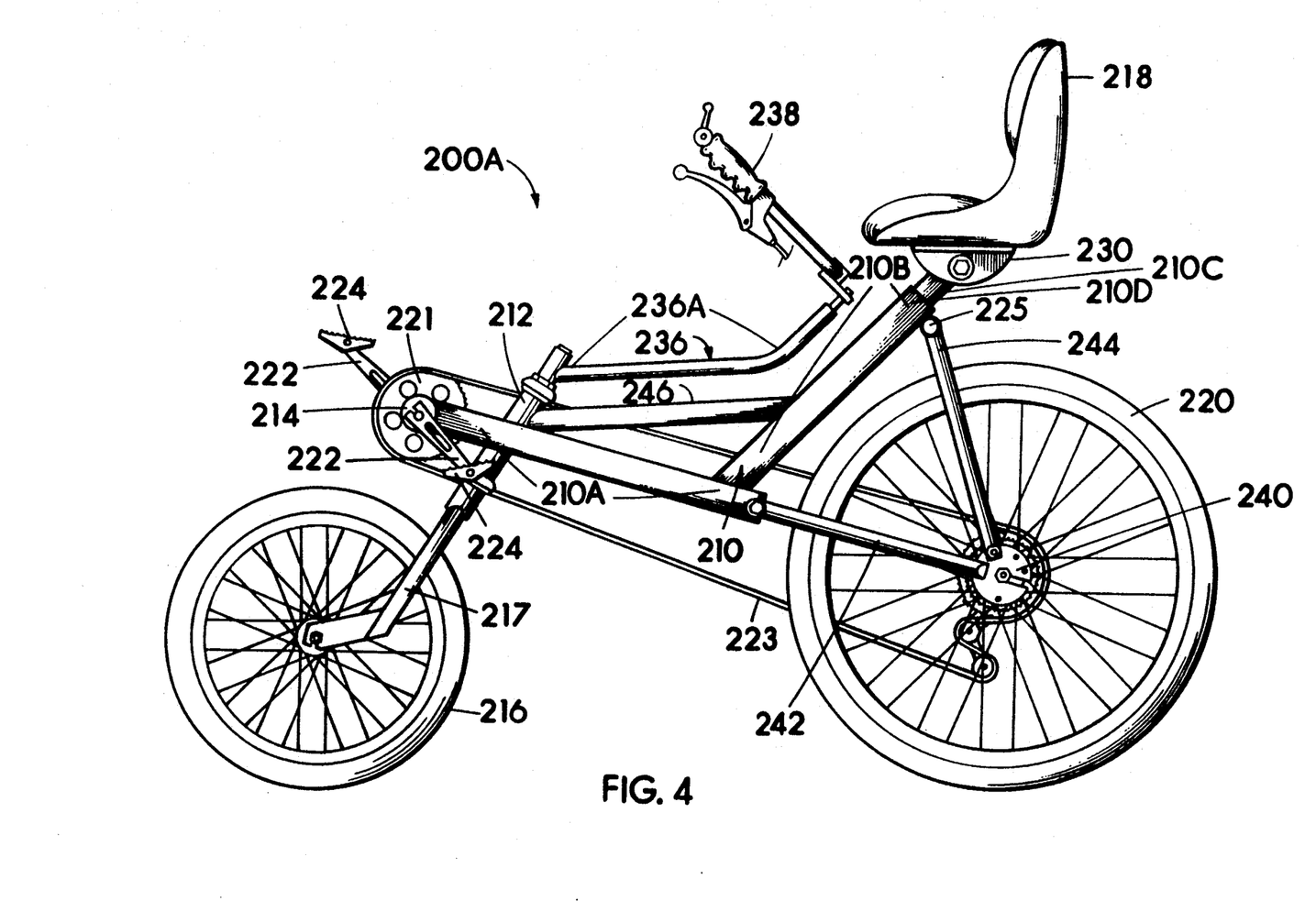
FIG. 4 is a left side view of a second embodiment of a semi-recumbent bicycle in accordance with the present invention.
Figure 5:
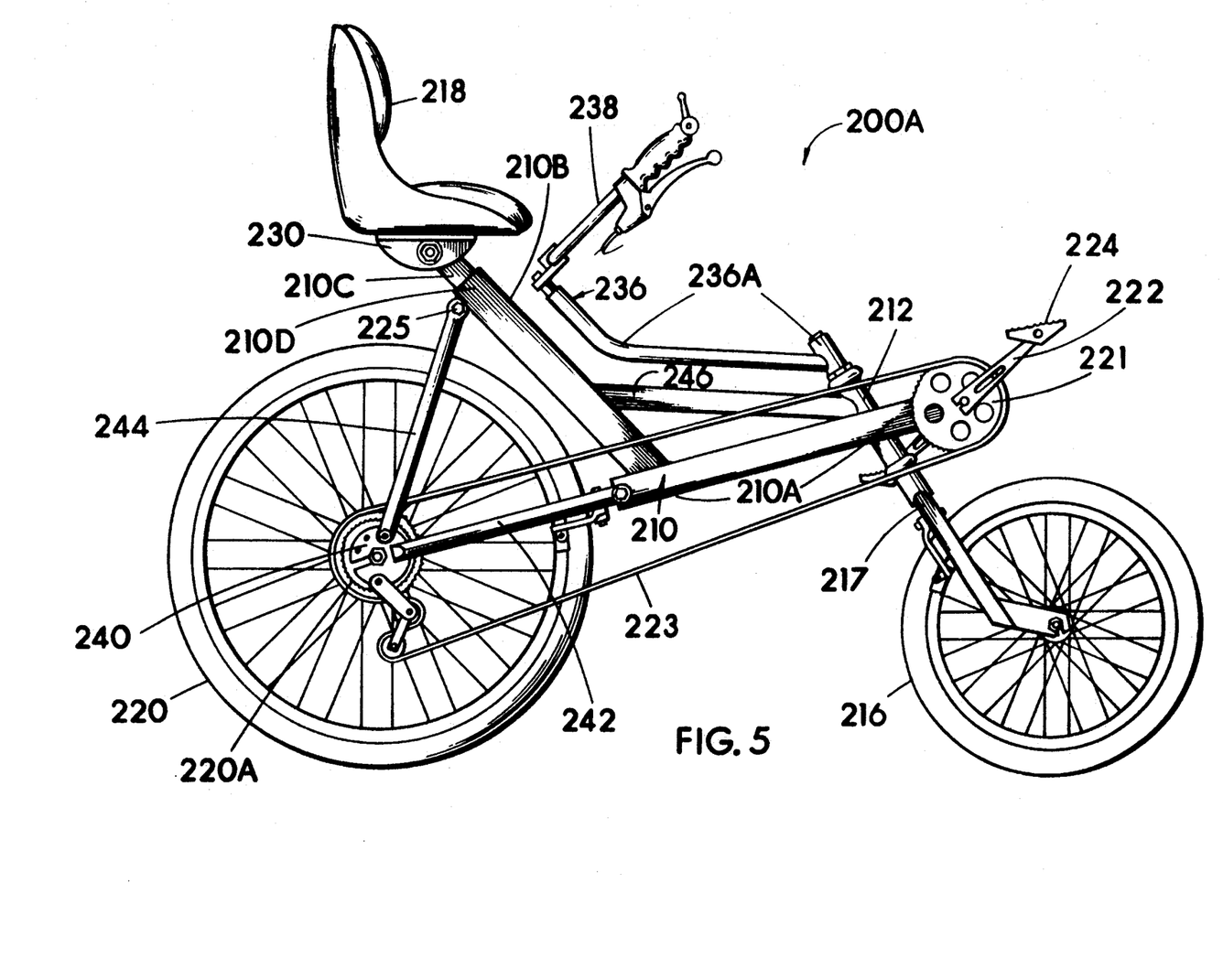
FIG. 5 is a right side view of the bike of FIG. 4.

Referring now mainly to FIGS. 4 and 5 to provide a brief description of second embodiment 200A which is primarily shown to exemplify that main tube need not be of round tubing, and need not be bent as with first embodiment 200 to be within the scope of the present invention. In bike 200A, multiple pieces of square tubing are welded or otherwise affixed together to provide the multiply angled main tube 210 having the generally horizontally disposed forward portion 210A and the substantially more vertically angled second portion 210B. Bike 200A further demonstrates that a strengthening brace such as brace 246 may be used if desired, and when properly placed still meet the goal of a low elevation placement of first portion 236A of steering stem 236. Additional braces and gussets may of course be used if desired provided they are carefully placed. When using materials which are of sufficient strength and rigidity, no bracing is needed. Multiple pieces of round tubing could be used in place of the square tubing for main tube 210 in bike 200A, and would appear quite similar to that of the main tube 210 of FIGS. 4 and 5.

Referring now mainly to FIG. 6 to provide a brief description of third embodiment 200B which is primarily shown to exemplify that a "live" or "suspended" rear wheel 220 may be used on a bicycle built in accordance with the present invention. Main tube 210 in this example is a square tube with a bend applied as opposed to round tubing with a bend applied as in first embodiment 200 to achieve the multiple angles or planes in main tube 210. In FIG. 6, a shock absorber 244A is used to replace each of the rigid seat stays 244 of embodiments 200 and 200A. Two shock absorbers 244A are used, a left and a right hand, one on each side of rear wheel 220 in this example, however only one side of this bike is shown. Chain stays 242 are pivotally connected at pivots 248 (one on each side of the bike) to main tube 210 using shouldered bolts as detailed in the reference patent, or using other suitable pivotal connections. Shock absorbers 244A are pivotally connected as indicated at 248 at each end of the shock absorber 244A. At the upper end of the shock absorbers 244A, a pair of tabs have been welded to outer portion 210D of main tube 210 below clamp 225 in order to accommodate the pivotal connections of the upper ends of the left and right hand shock absorber 244A. A telescopic steering stem 236 is also shown for example in FIG. 6.

With any of the embodiments such as 200, 200A, or 200B in accordance with the present invention, bolt-in seat stays and chain stays which may be easily replaced with stays of different lengths in order to change the bike configuration pertaining to wheel base, generally overall height of the bike, or even the planes in which main tube 210 exists, may of course be used if desired as is taught in the reference patent. Changing the configuration of a given bike through changing the lengths of the seat stays and or chain stays can produce a variety of handling characteristics, with some of the characteristics being more suitable for certain types of riding such as street riding, off-road riding or racing for example, and often the angle of handlebar 238 and the position of the seat 218 is also changed to provide different handling characteristics.

Figure 10:
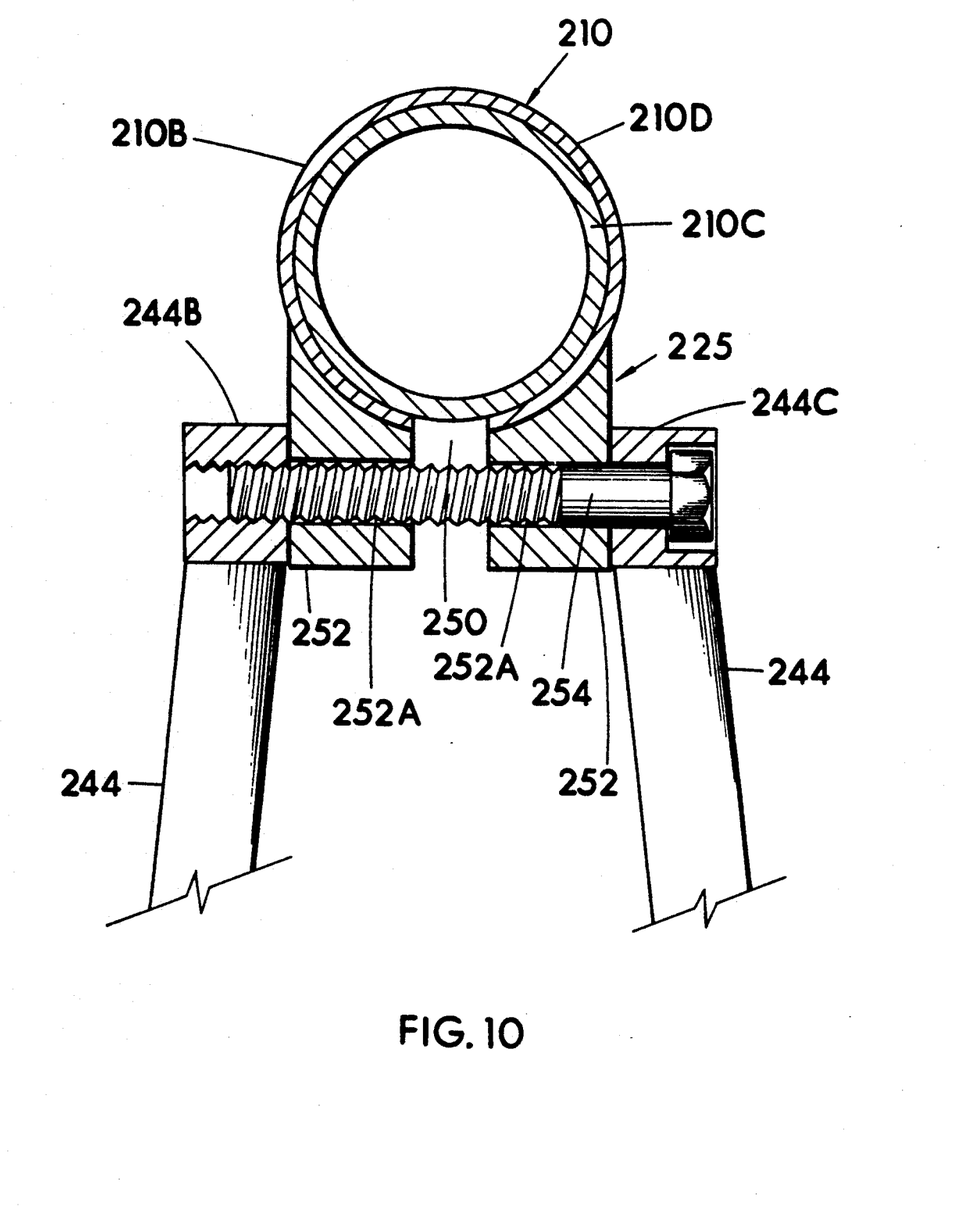
FIG. 10 is a partial cross-sectional view illustrating an example of attaching seat stays in a manner which also serves to securely clamp a telescopic main tube.

Referring now mainly to FIG. 10 to provide a brief description of clamp 225. Clamp 225 is a combined seat stay attachment and releasible clamp. Clamp 225 is at the top end of the outer portion 210D of main tube 210 in second portion 210B thereof, and is used to render the inner member 210C stationary relative to the outer portion 210D when the length of main tube 210 is to satisfaction. Although several other clamp arrangements could be used, and the seat stays 244 need not be attached to main tube 210 in a manner which also serves to render inner member 210C stationary relative to the outer portion 210D, the structure shown in FIG. 10 is an efficient arrangement for attaching the upper collars of the rigid seat stays 244 to second portion 210B of main tube 210. In FIG. 10, a short split 250 is provided in outer portion 210D. The length of the split 250 is two or three inches as may be seen in FIG. 8. Two tabs 252, one on each side of the split 250 are welded or otherwise attached to outer portion 210D. Each of the tabs 252 include an unthreaded hole 252A therethrough and in alignment with one another so as to be able to receive a single bolt 254. The upper end of each of the seat stays 244 includes an affixed collar, with one collar 244B having a threaded hole therethrough so as to be able to accept the threads of bolt 254, and the other collar designated 244C includes an unthreaded hole therethrough to allow passage of the shank of bolt 254. Collar 244C is shown with a recess to allow recessing of the head of bolt 254. To assemble, the shank of bolt 254 is passed through collar 244C, through both tabs 252 and threadably engaged with the threaded bore of collar 244B and tightened. The tightening of bolt 254 clamps outer portion 210D onto inner member 210C, and also secures the upper ends of seat stays 244 to second portion 210B of main tube 210 in a non-pivotal manner.

Figure 11:
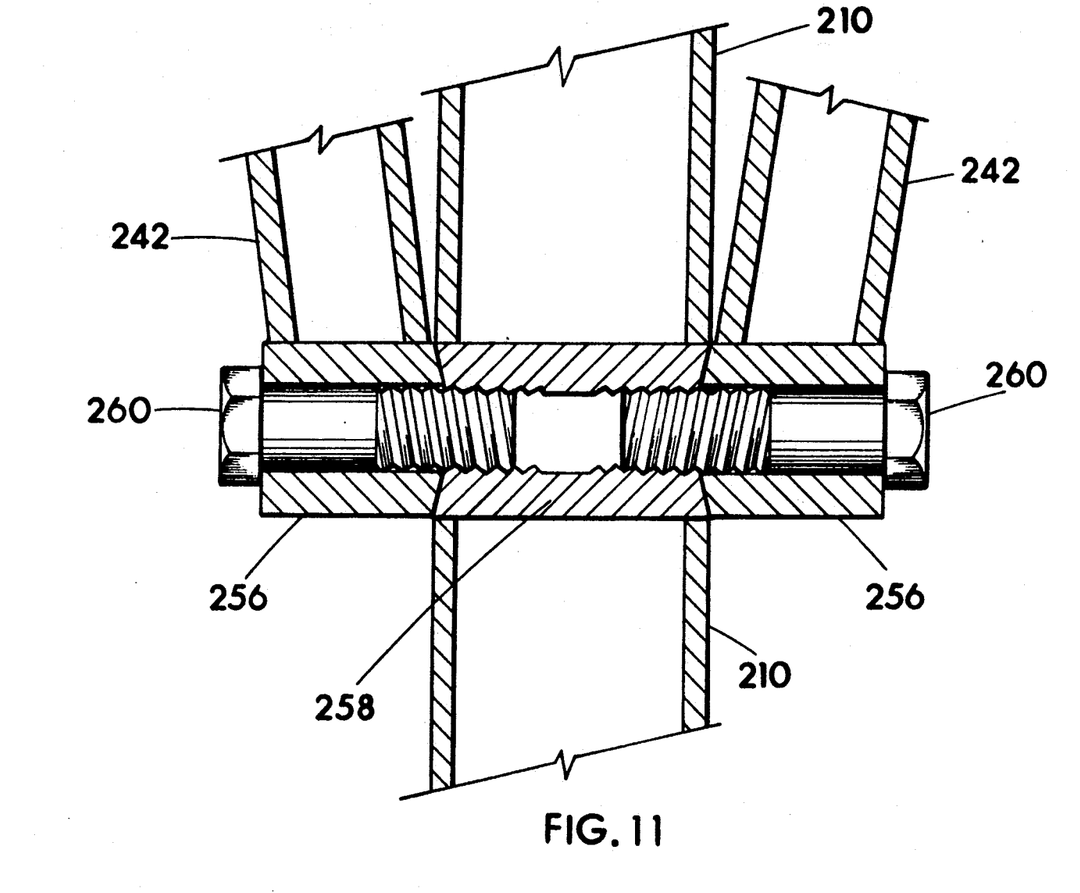
FIG. 11 is a partial cross-sectional view illustrating one suitable attachment structure for attaching chain stays to a main tube of my bicycle.

Referring now mainly to FIG. 11 to provide a brief description of one possible suitable attachment structure for attaching the forward end of each of the chain stays 242 in a non-pivotal manner to main tube 210. The attachment of the forward ends of each of the chain stays 242 will normally be made in or closely adjacent the bend or angle change portion main tube 210 of any my bicycles in accordance with the present invention as may be seen in FIGS. 2, 4, 6, but again the forward ends of the chain stays 242 could be attached elsewhere on the main framework of the bike is disclosed in the reference patent. Other attachment methods or structures may of course be used such as is disclosed in the reference patent, however that which is shown in FIG. 11 of this disclosure is seen to be an efficient structure. FIG. 11 is a partial cross-sectional view illustrating a tubular main tube 210 made of metal, wherein a hole has been drilled or otherwise fashioned transversely through the tube 210. Inserted into the drilled hole is centrally bored and threaded spacer 258. Spacer 258 is of a length which is generally equivalent to the width of the main tube 210 as shown in the drawing. Affixed to the forward terminal ends of each of the chain stay 242 are collars 256 each having an unthreaded bore therethrough. As may be seen in the drawing, the exposed ends of spacer 258 may be concavely fashioned, and one inward side of each of the collars 256 may be likewise convexly fashioned so as to form a self-centering arrangement. The shank of a bolt 260 is passed through each collar 256 and into threaded engagement with the internal threads of spacer 258 to fasten the forward ends of the chain stays 242 in place. Spacer 258 may be welded or pressed in place and retained by friction in the hole in main tube 210, or may be left loose and readily removable if desired.

Although I have described preferred structures of the invention, it should be understood that the specific details are just that, "preferred" structures given for example to those skilled in the art. Many changes in the specific structures described may obviously be made without departing from the scope of the invention as reflected by the appended claims.

What I claim as my invention is:

1. A semi-recumbent bicycle structured with a relatively low height whereat a person straddles an elongated steering stem during mounting of said bicycle, and on which a rider sits on a seat having back support in a semi-recumbent position while riding said bicycle, said bicycle comprising in combination;
    a generally vertically oriented head tube, a downward end of said head tube having wheel attachment means rotatably affixed thereto, said wheel attachment means retaining a rotatably affixed front wheel, said head tube having a rotatably affixed said steering stem extending from an upper end thereof with at least a first elongated portion of said steering stem extending rearward in a generally horizontally disposed plane, a handlebar attached to a rearward end of said steering stem, said steering stem and said head tube including means for rotating said wheel attachment means and said front wheel with movement of said handlebar by a rider for steering of said bicycle;
    an elongated main tube affixed at a forward portion thereof to said head tube, said main tube extending rearward from said head tube, said main tube comprising an inner member telescopically positioned within an outer member with the telescopic structure adapted to provide length adjustability of said main tube, a releasable clamping means affixed to said main tube and adapted to secure said inner member and said outer member stationary relative to one another;
    said seat affixed to an upper rearward end of said main tube, said length adjustability of said main tube providing means for selective positioning of said seat, said seat being positioned adjacent said handlebar so that with a rider sitting on said seat said handlebar originates underneath the rider's legs and said handlebar extends outward and upward to provide a portion of said handlebar disposed adjacent the exterior of each of the rider's legs;
    said head tube with said main tube attached thereto defining a main framework of said bicycle, said head tube and said main tube adjacent said head tube defining a forward portion of said main framework;
    a rotatably attached rear wheel having an axle supported in axle drop-out plates with the axle drop-out plates affixed to and supported by seat stays and chain stays, said seat stays and chain stays being attached to said main framework of said bicycle so as to define a triangulated support structure for said rear wheel, said rear wheel positioned generally below said seat, at least one rear sprocket affixed to rotate with said rear wheel;
    a manual powering assembly providing means to allow powering of said bicycle by a rider's legs with the rider sitting on said seat in a semi-recumbent position, said powering assembly comprising a bottom bracket affixed to said forward portion of said main framework, said bottom bracket supporting two oppositely disposed rotatable crank arms, each of said crank arms having a rotatably affixed foot pedal attached thereto, at least one front sprocket affixed to rotate with rotation of said crank arms, said front sprocket connected by a drive chain to said rear sprocket to provide means for rotating said rear wheel with rotation of said crank arms;
    said bicycle further characterized in that said main tube extends rearward from said head tube in a first plane and then changes angle and extends upward and rearward to above said rear wheel in a second plane, the angle change in said main tube into said second plane occurring between said head tube and said rear wheel, said second plane of said main tube being a plane which is substantially more vertically oriented relative to said first plane of said main tube; said main tube being in said first and second planes providing clearance for at least said first elongated portion of said steering stem to be placed in a generally horizontally disposed plane to provide the relatively low height for a person to straddle during mounting of said bicycle.

2. A bicycle according to claim 1 wherein said seat is attached to said main tube by attachment means having means providing for selectively adjusting the position of said seat independent of said selective positioning of said seat provided by said length adjustability of said main tube, and thereby independent horizontal and vertical adjustments to the position of said seat relative to said pedals may be accomplished.

3. A bicycle according to claim 2 wherein said forward portion of said main tube extends forward a distance beyond said head tube to above said front wheel, and said bottom bracket is positioned in the forward extending portion of said main tube forward of said head tube;

said bottom bracket supporting said crank arms with attached pedals being positioned relative to said front wheel so as to provide clearance between said front wheel and said crank arms with said pedals when said crank arms are rotated and said front wheel is turned for steering.

4. A bicycle according to claim 3 wherein said inner member and said outer member of said main tube are generally rectangular tubing so as to prohibit axial rotation of said inner member within said outer member, and further wherein said first plane of said main tube is a relatively horizontal plane and said second plane of said main tube is a plane extending vertically in a range between 30 degrees and 70 degrees from horizontal.

5. A bicycle according to claim 3 wherein said main tube is a welded assembly of multiple pieces of tubing to provide said main tube in said first and second planes, and further wherein said first plane of said main tube is a relatively horizontal plane and said second plane of said main tube is a plane extending vertically in a range between 30 degrees and 70 degrees from horizontal.

6. A bicycle according to claim 3 wherein said inner member and said outer member of said main tube are round tubing, and a bend is applied to said round tubing to provide said main tube in said first and second planes.

7. A bicycle according to claim 6 wherein said first plane of said main tube is a relatively horizontal plane and said second plane of said main tube is a plane extending vertically in a range between 30 degrees and 70 degrees from horizontal.

8. A bicycle according to claim 2 wherein said seat stays and said chain stays are attached to said main framework by removable attachment means adapted to allow removal and attachment of differently sized said seat stays and said chain stays to said main framework.

9. A bicycle according to claim 8 wherein said seat stays include shock absorbtion means, and said chain stays are pivotally attached to said main framework.

* * * * *